(12) United States Patent
Miau et al.

(10) Patent No.: US 8,303,555 B2
(45) Date of Patent: Nov. 6, 2012

(54) SOFT COLLECTOR FOR A NEGATIVE PRESSURE WOUND THERAPY SYSTEM AND ITS COMBINATION

(75) Inventors: Luo-Hwa Miau, Tu-Cheng (TW); Jhy-Wen Wu, Tu-Cheng (TW); Jen-Chien Chien, Tu-Cheng (TW); Li-Ling Li, Tu-Cheng (TW); Nan-Kuang Yao, Tu-Cheng (TW)

(73) Assignee: Apex Medical Corp., Tu-Cheng, Taipei Hsien (TW)

( * ) Notice: Subject to any disclaimer, the term of this patent is extended or adjusted under 35 U.S.C. 154(b) by 161 days.

(21) Appl. No.: 12/872,990

(22) Filed: Aug. 31, 2010

(65) Prior Publication Data

US 2012/0053543 A1    Mar. 1, 2012

(51) Int. Cl.
*A61M 1/00*    (2006.01)
(52) U.S. Cl. .................. 604/321; 604/317; 604/319
(58) Field of Classification Search .................. None
See application file for complete search history.

(56) References Cited

U.S. PATENT DOCUMENTS

| | | | |
|---|---|---|---|
| 4,388,922 A | 6/1983 | Telang | |
| 6,152,902 A * | 11/2000 | Christian et al. | 604/320 |
| 2005/0137539 A1 | 6/2005 | Biggie et al. | |
| 2007/0265586 A1 * | 11/2007 | Joshi et al. | 604/313 |
| 2009/0292263 A1 | 11/2009 | Hudspeth et al. | |
| 2010/0125258 A1 | 5/2010 | Coulthard et al. | |
| 2010/0160881 A1 * | 6/2010 | Lin et al. | 604/327 |

FOREIGN PATENT DOCUMENTS

| | | | |
|---|---|---|---|
| EP | 1566188 A1 | | 8/2005 |
| GB | 2259255 A | * | 3/1993 |
| GB | 2452393 A | | 3/2009 |
| GB | 2466321 A | | 6/2010 |
| WO | 95/01192 A2 | | 1/1995 |
| WO | 2007133618 A2 | | 11/2007 |
| WO | 2009077722 A1 | | 6/2009 |
| WO | 2009124100 A1 | | 10/2009 |
| WO | 2010054066 A2 | | 5/2010 |

* cited by examiner

*Primary Examiner* — Jackie Ho
*Assistant Examiner* — Joshua Lee
(74) *Attorney, Agent, or Firm* — patenttm.us

(57) ABSTRACT

A collector for a negative pressure wound therapy system has a soft collecting bag with a gas-permeable unit and a liquid absorber. The collecting bag is connected to a wound-dressing unit via an inlet connecting set and is connected to a sensor assembly via a detecting connecting set. With the soft collecting bag, the collector occupies less volume. By the gas-permeable unit and the liquid absorber, the liquid and gas entering into the collecting bag quickly isolate. Moreover, multiple collectors connect in series to form a collector combination to reduce the frequency to replace the collector combination so that a longer usage time of the collector combination is available.

12 Claims, 3 Drawing Sheets

SOFT COLLECTOR FOR A NEGATIVE PRESSURE WOUND THERAPY SYSTEM AND ITS COMBINATION

BACKGROUND OF THE INVENTION

1. Field of the Invention

The present invention relates a collector, especially to a soft collector used for a negative pressure wound therapy system.

2. Description of the Prior Arts

Negative pressure wound therapy utilizes wound sheets, soft suction pads, or biocompatible pore materials to attach on the wounds and connect to a vacuum pump. The vacuum pump creates negative pressure in the wound to extract the pus and infection subjects and to draw the healthy tissue fluid so that a moist therapy environment is maintained. Therefore, the blood circulation around the wound is promoted to accelerate wound healing.

A conventional negative pressure wound therapy system has a conventional collector connecting to a front end of the vacuum pump to extract the pus and the infection subjects into the collector. Because the vacuum pump needs to create a negative pressure environment in the wound through the conventional collector, the conventional collector must be a rigid container to avoid deforming. However, the rigid container occupies a fixed space. Therefore, the conventional collector is not convenient to be stowed and be carried. Moreover, the conventional collector with full pus and infection subjects needs to be treated as a medical waste. The medical wastes have specialized treatment so that the conventional collectors, which are rigid containers, increase the volume of the medical wastes.

To overcome the shortcomings, the present invention provides a soft collector for a negative pressure wound therapy system and its combination to mitigate or obviate the aforementioned problems.

SUMMARY OF THE INVENTION

The main objective of the present invention is to provide a soft collector for a negative pressure wound therapy system to be carried and disposed conveniently. The collector has a soft collecting bag with a gas-permeable unit and a liquid absorber. The collecting bag is connected to a wound-dressing unit via an inlet connecting set and is connected to a sensor assembly via a detecting connecting set. With the soft collecting bag, the collector occupies less volume. By the gas-permeable unit and the liquid absorber, the liquid and gas entering into the collecting bag quickly isolate. Moreover, multiple collectors connect in series to form a collector combination to reduce the frequency to replace the collector combination so that a longer usage time of the collector combination is available.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
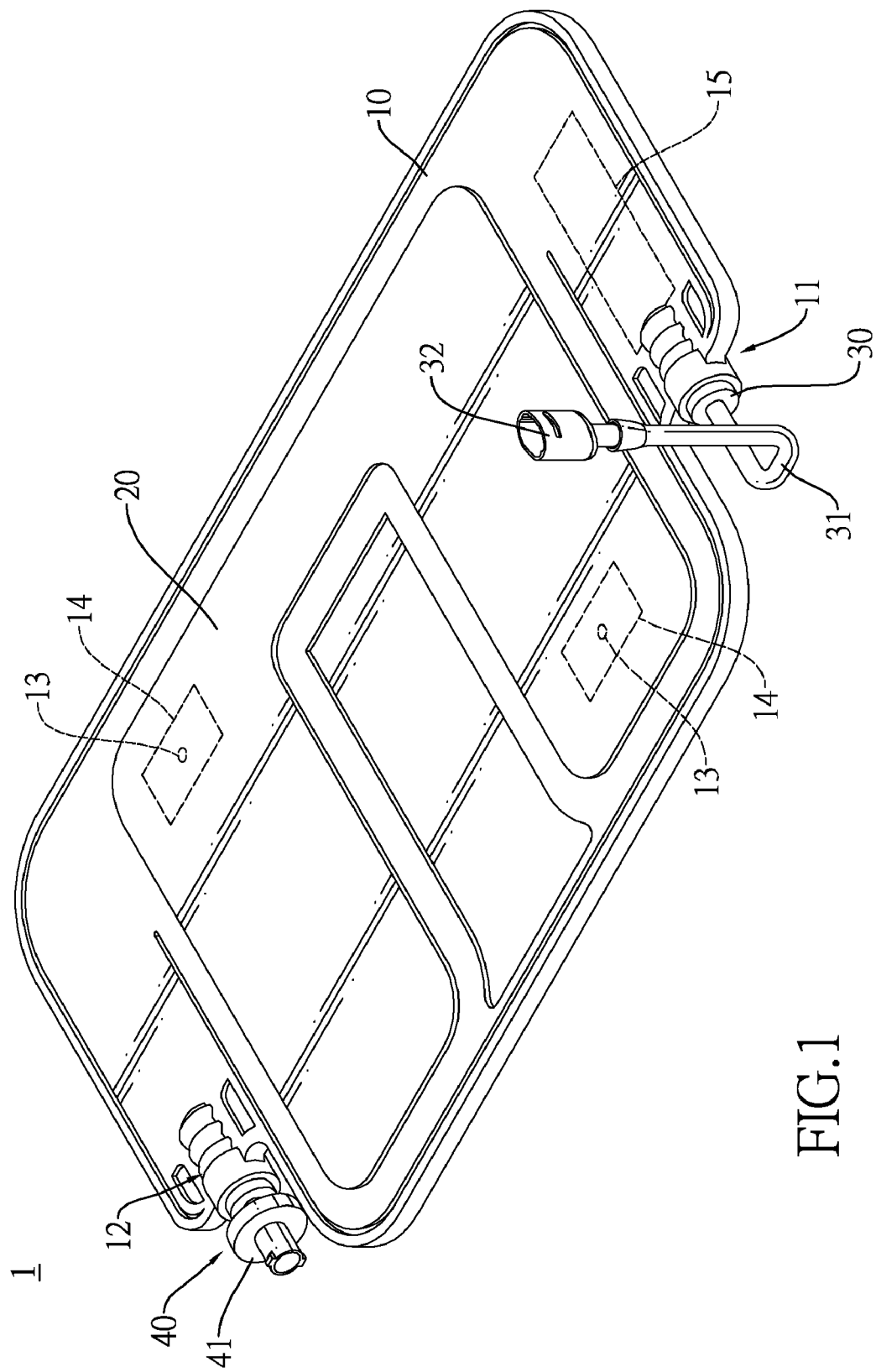
FIG. 1 is a perspective view of a soft collector for a negative pressure wound therapy system in accordance with the present invention.

With reference to FIG. 1, a soft collector 1 for a negative pressure wound therapy system in accordance with the present invention comprises a collecting bag 10, an absorber 20, an inlet connecting set 30 and a detecting connecting set 40.

The collecting bag 10 is a soft and flexible bag and has a front end opening 11, a rear end opening 12, a top side, a bottom side, a check valve 15 and two gas permeable units. The check valve 15 is mounted in the front end opening 11 to stop the liquid in the collecting bag 10 from flowing back. Each gas permeable unit attached to a corresponding side of the collecting bag 10 and comprises a through hole 13 and a gas permeable membrane 14. The through hole 13 is formed through the corresponding side of the collecting bag 10. The gas permeable membrane 14 is attached to an inside surface of the corresponding side and covers the through hole 13 to allow the gas in the collecting bag 10 to dissipate out without leaking the liquid inside the collecting bag. In a preferred embodiment, the collecting bag 10 has two gas permeable units attached separately and respectively to the top and bottom sides of the collecting bag and arranged separately and diagonally with respect to each other to advance dissipation of the gas in the collecting bag 10.

The liquid absorber 20 is mounted in the collecting bag 10. In a preferred embodiment, the liquid absorber 20 is attached securely in the collecting bag 10 by high frequency welding. The liquid absorber 20 is made of polymer absorbing materials such as polyvinyl alcohol (PVA), super absorbent polymer (SAP) and so on. The liquid absorber 20 takes in the liquid in the collecting bag 10 and may be U-shaped.

The inlet connecting set 30 is mounted in the front end opening 11 of the collecting bag 10 and comprises a connecting tube 31 and a connector 32 joining together. The connecting tube 31 is inserted in the front end opening 11.

The detecting connecting set 40 is mounted in the rear end opening 12 of the collecting bag 10 and comprises a gas permeable connector 41 inserted into the rear end opening 12 to allow gas to pass through so that the positive pressure in the collecting bag 10 is detectable.

Figure 2:
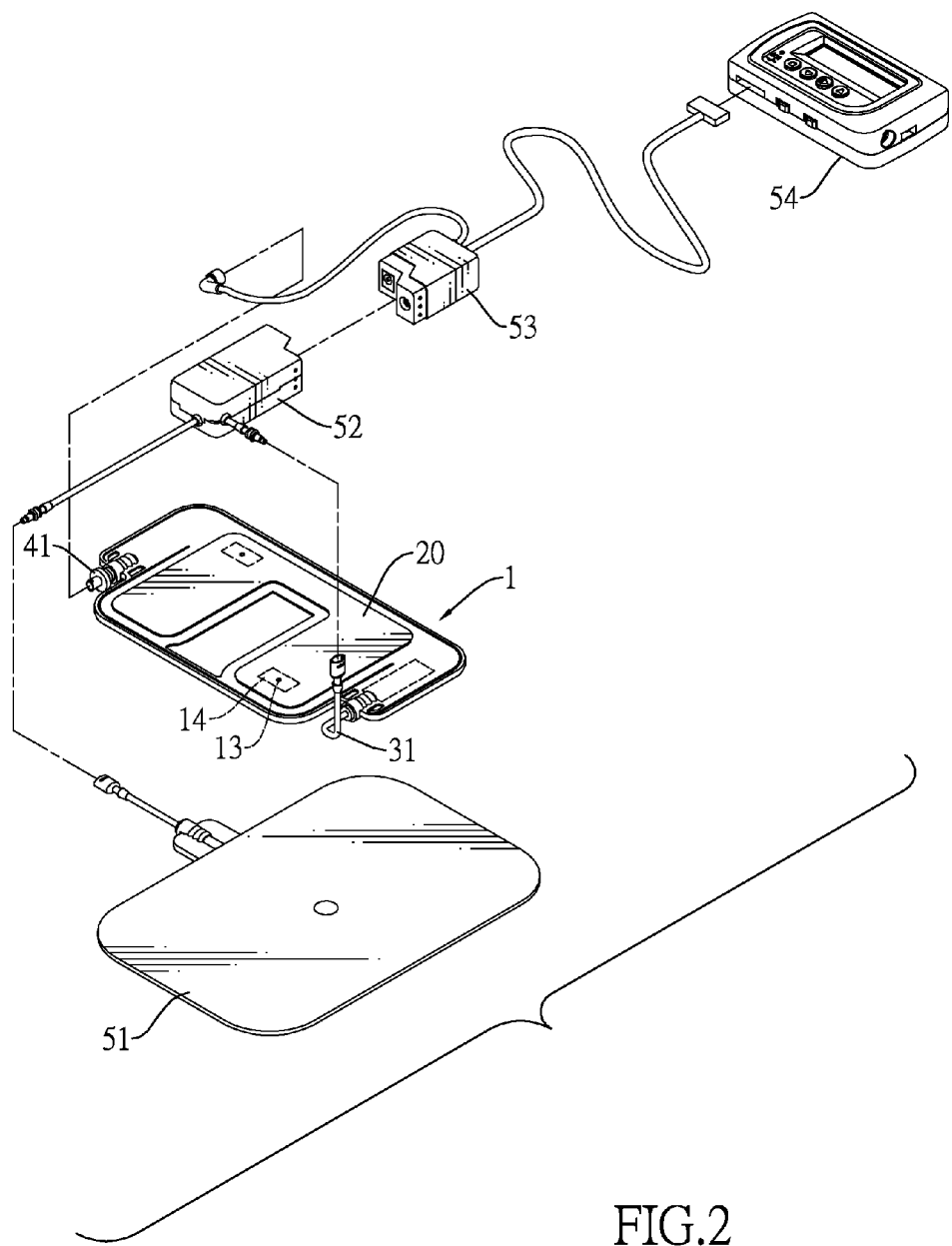
FIG. 2 is an exploded perspective view of the negative pressure wound therapy system with the soft collector in FIG. 1.

With reference to FIG. 2, the soft collector 1 as described is a part of the negative pressure wound therapy system. The connector 32 is connected to the outlet of the actuator 52. The inlet of the actuator 52 is connected to the wound-dressing unit 51. The gas permeable connector 41 is connected to the sensor assembly 53. The sensor assembly 53 joins to the actuator 52 and electrically connects to the controller 54. Since the actuator 52 is connected between the wound-dressing unit 51 and the soft collector 1, the actuator 52 only creates a negative environment in the wound, and the soft collector 1 is a positive pressure environment.

The wound-dressing unit 51 is attached to the user's wound. When the negative pressure wound therapy system is started, the actuator 52 creates a negative environment in the wound to extract pus and infection subjects. The pus and infection subjects pass through the actuator 52 and flow into the collecting bag 10. The liquid in the pus and the infection subjects are absorbed by the liquid absorber 20 to separate the liquid and the gas. The gas dissipates out of the collecting bag 10 through the gas permeable membrane 14. Therefore, the rest space in the collecting bag 10 can contain more liquid.

Furthermore, because most of the liquid is absorbed in the liquid absorber 20, the rest space in the collecting bag 10 acts as cushion to keep the collecting bag 10 from breaking when over stressed.

The soft collector 1 as described has other following advantages. With a soft collecting bag 10, the soft collector 1 is convenient to be stowed and carried and reduces the wasted volume. Moreover, because of the check valve 15 and the insertion of the connecting sets 30, 40, the liquid in the collecting bag 10 does not leak so that the collecting bag 10 is available to be put in any way such as upside-down.

Figure 3:
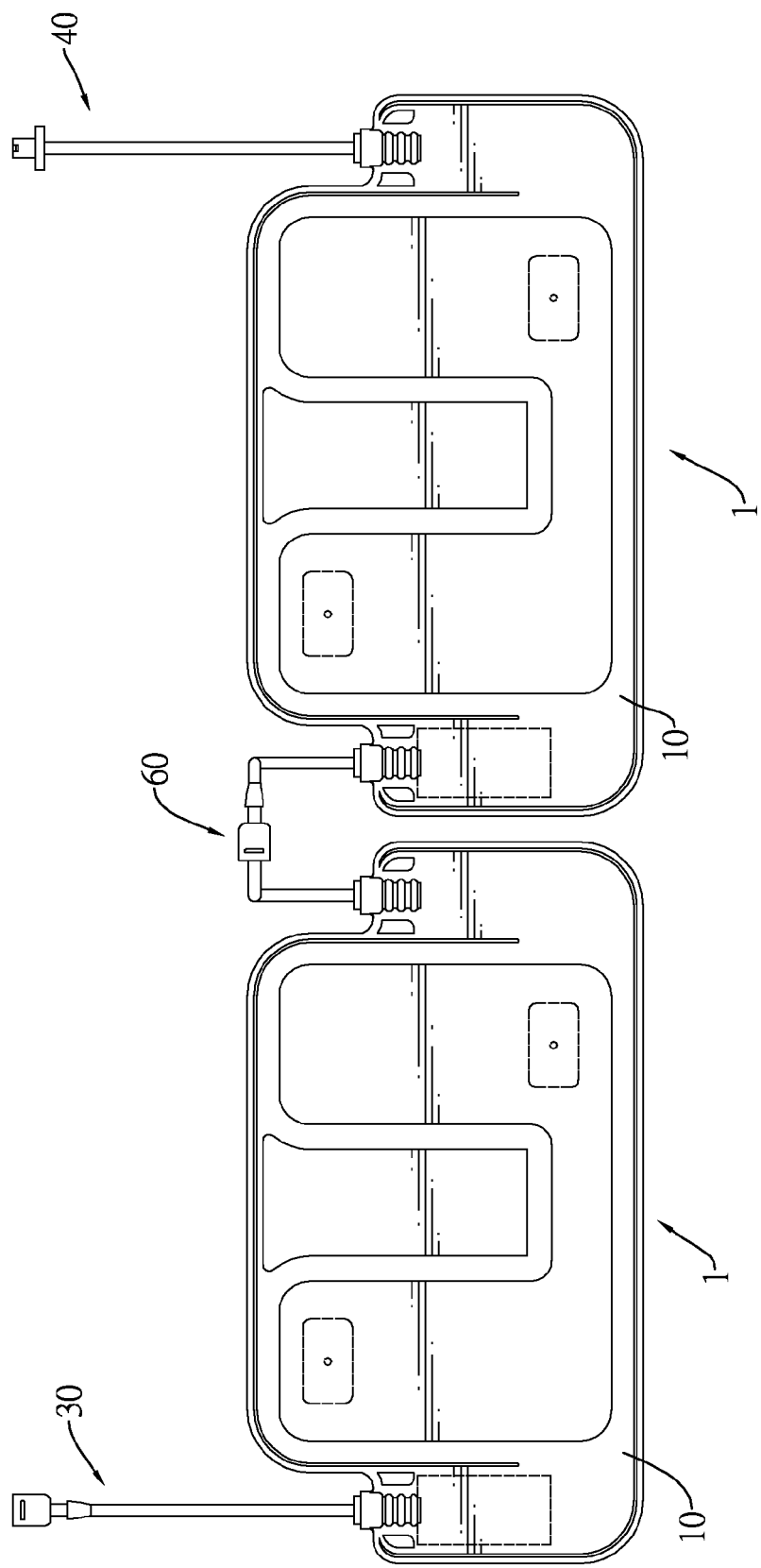
FIG. 3 is a top view of a collector combination for a negative pressure wound therapy system in accordance with the present invention.

With reference to FIG. 3, a collector combination in accordance with the present invention comprises multiple soft collectors 1. The soft collectors 1 connect in series to form a continuous flowing passage. Adjacent soft collectors 1 connect to each other by an intermediary connecting set 60. The collecting bag 10 of the first soft collector 1 in the flowing passage connects to the inlet connecting set 30 to connect to the wound-dressing unit. The collecting bag 10 of the last soft collector 1 in the flowing passage connects to the detecting connecting set 40 to connect to the sensor assembly. With the series connection, the user can use multiple collectors to contain more liquid. Therefore, the replacing frequency of the collector combination is reduced and the negative pressure wound therapy system has longer usage time.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A soft collector for a negative pressure wound therapy system comprising:
    a collecting bag being soft and flexible and having
        a front end opening;
        a rear end opening;
        a top side;
        a bottom side;
        a check valve mounted in the front end opening to prevent backflow; and
        two gas permeable units attached separately and respectively to the top and bottom sides of the collecting bag and arranged diagonally with respect to each other, each gas permeable unit comprising
            a through hole formed through corresponding one of the top and the bottom sides of the collecting bag; and
            a gas permeable membrane attached to an inside surface of corresponding one of the top and the bottom sides and covering the through hole;
    a liquid absorber mounted in the collecting bag;
    an inlet connecting set mounted in the front end opening of the collecting bag; and
    a detecting connecting set mounted in the rear end opening of the collecting bag and having a gas permeable connector inserted into the rear end opening.

2. The soft collector as claimed in claim 1, wherein the liquid absorber is made of polyvinyl alcohol.

3. The soft collector as claimed in claim 1, wherein the liquid absorber is made of super absorbent polymer.

4. The soft collector as claimed in claim 1, wherein the liquid absorber is attached securely in the collecting bag.

5. The soft collector as claimed in claim 4, wherein the liquid absorber is U-shaped in cross section.

6. The soft collector as claimed in claim 1, wherein the inlet connecting set comprises
    a connecting tube inserted into the front end opening; and
    a connector joined to the connecting tube.

7. A collector combination for a negative pressure wound therapy comprising:
    multiple soft collectors connecting in series to form a continuous flowing passage, each soft collector comprising
        a collecting bag being soft and flexible and having
            a front end opening;
            a rear end opening;
            a top side;
            a bottom side;
            a check valve mounted in the front end opening to prevent backflow; and
            two gas permeable units attached separately and respectively to the top and bottom sides of the collecting bag and arranged diagonally with respect to each other, each gas permeable unit comprising
                a through hole formed through corresponding one of the top and the bottom sides of the collecting bag; and
                a gas permeable membrane attached to an inside surface of corresponding one of the top and the bottom sides and covering the through hole; and
        a liquid absorber mounted in the collecting bag;
    an inlet connecting set mounted in the front end opening of the collecting bag of a first collector in the flowing passage;
    and
    a detecting connecting set mounted in the rear end opening of the collecting bag of a last collector in the flowing passage and having a gas permeable connector inserted into the rear end opening,
    wherein the collecting bags of adjacent collectors connect to each other by an intermediary connecting set.

8. The collector combination as claimed in claim 7, wherein the liquid absorbers are made of polyvinyl alcohol.

9. The collector combination as claimed in claim 7, wherein the liquid absorbers are made of super absorbent polymer.

10. The collector combination as claimed in claim 7, wherein the liquid absorber of each soft collector is attached securely in the collecting bag.

11. The collector combination as claimed in claim 10, wherein the liquid absorbers are U-shaped in cross section.

12. The collector combination as claimed in claim 7, wherein the inlet connecting set comprises
    a connecting tube inserted into the front end opening of the collecting bag of the first soft collector; and
    a connector joined to the connecting tube.

* * * * *